(12) United States Patent
Hengesbach et al.

(10) Patent No.: US 9,382,660 B2
(45) Date of Patent: Jul. 5, 2016

(54) METHOD FOR AUTOMATICALLY DETERMINING STICKIES IN A RECYCLED FIBRE PROCESS

(71) Applicant: Stora Enso Oyj, Helsinki (FI)

(72) Inventors: Peter Hengesbach, Willich (DE); Roman Krause, Leipzig (DE)

(73) Assignee: Stora Enso Oyj, Helsinki (FI)

( * ) Notice: Subject to any disclaimer, the term of this patent is extended or adjusted under 35 U.S.C. 154(b) by 0 days.

(21) Appl. No.: 14/391,514

(22) PCT Filed: Apr. 16, 2013

(86) PCT No.: PCT/EP2013/001124
§ 371 (c)(1),
(2) Date: Oct. 9, 2014

(87) PCT Pub. No.: WO2013/156147
PCT Pub. Date: Oct. 24, 2013

(65) Prior Publication Data
US 2015/0075741 A1    Mar. 19, 2015

(30) Foreign Application Priority Data

Apr. 16, 2012  (EP) .................... 12002648

(51) Int. Cl.
*D21C 5/02* (2006.01)
*D21H 21/02* (2006.01)
*D21H 23/78* (2006.01)

(52) U.S. Cl.
CPC .................. *D21C 5/02* (2013.01); *D21H 21/02* (2013.01); *D21H 23/78* (2013.01)

(58) Field of Classification Search
CPC ............ D21C 5/02; D21C 9/08; D21H 21/02; D21H 23/78; Y10S 210/928; D21D 5/04; G01N 33/343; G01N 33/346
See application file for complete search history.

(56) References Cited

U.S. PATENT DOCUMENTS

| 3,441,130 | A | * | 4/1969 | Sisson | B01D 37/00 162/55 |
| 3,992,249 | A | * | 11/1976 | Farley | D21C 9/086 162/168.1 |
| 4,956,051 | A | | 9/1990 | Moreland | 162/199 |
| 5,080,759 | A | * | 1/1992 | Buzby | D21C 5/022 162/147 |
| 5,338,401 | A | * | 8/1994 | Naddeo | D21C 5/02 162/6 |
| 5,540,814 | A | | 7/1996 | Curtis et al. | 162/5 |
| 6,572,733 | B1 | | 6/2003 | Banerjee | 162/50 |
| 7,407,561 | B2 | * | 8/2008 | Song | D21H 21/02 162/147 |
| 8,048,262 | B2 | * | 11/2011 | Jiang | D21H 21/02 162/9 |
| 2004/0256071 | A1 | * | 12/2004 | Huhtamaki | D21B 1/026 162/189 |
| 2009/0133845 | A1 | * | 5/2009 | Huhtelin | D21C 5/02 162/4 |
| 2015/0075741 | A1 | * | 3/2015 | Hengesbach | D21H 21/02 162/198 |

FOREIGN PATENT DOCUMENTS

| EP | 1975310 A1 | 10/2008 | |
| EP | 2410023 A1 | 1/2012 | |
| FI | WO 2013156147 A1 * | 10/2013 | ............ D21H 21/02 |
| WO | WO 00/31499 | 6/2000 | |
| WO | WO 00/45156 | 8/2000 | |
| WO | WO 02/086230 | 10/2002 | |

OTHER PUBLICATIONS

International Search Report from PCT/EP2013/001124 mailed May 28, 2013.
International Preliminary Report on Patentability and Written Opinion from PCT/EP2013/001124 completed Jun. 25, 2014.

* cited by examiner

*Primary Examiner* — Jose Fortuna
(74) *Attorney, Agent, or Firm* — Licata & Tyrell P.C.

(57) ABSTRACT

The invention relates to a method and a system for continuously and automatically determining sticky levels in a process for producing recycled fiber pulp utilizing near-infrared (NIR) spectroscopy in combination with one or more automated sheet former(s).

13 Claims, 5 Drawing Sheets

METHOD FOR AUTOMATICALLY DETERMINING STICKIES IN A RECYCLED FIBRE PROCESS

This application is the national stage under 35 U.S.C. §371 of PCT International Application No. PCT/EP2013/001124, filed Apr. 16, 2013, which claims priority from EP 12002648.9, filed Apr. 16, 2012, the contents of which are incorporated herein by reference in their entireties.

TECHNICAL FIELD

The invention relates to a method and a system for continuously and automatically determining sticky levels in a process for producing recycled fibre pulp utilizing near-infrared (NIR) spectroscopy in combination with one or more automated sheet former(s).

BACKGROUND

During the last two decades environmental and economical demands have contributed to the increased use of recycled fibers in the production of paper. In the converting of paper raw material into pulp, recovered paper is broken down to fibers in a pulping process. In the pulping process, the paper is torn up and treated with chemicals at enhanced temperature. The fiber suspension leaving the pulper is further treated in several steps, including e.g. screening, flotation and/or centrifugal cleaning, and it may be bleached by the addition of oxidative and/or reductive bleaching agents.

One problem with the use of recycled fibers is the variety of contaminants in recovered paper. Many of these contaminants adhere to fibers and fillers therefore may cause problems during the recycling process. One of such contaminants are "stickies". Stickies are grouped into primary and secondary stickies depending on their source and formation process, respectively. Primary stickies are introduced with the recovered paper while secondary stickies are produced by physicochemical processes during the process for producing recycled fibre pulp. Stickies may originate from a variety of different sources such as adhesives applications from various paper products, hotmelts from bookbinders and carton sealants, self adhesive labels, polymeric binders from coated paper and ink residues. Stickies typically are classified as hot melts, pressure-sensitive adhesives (PSAs), latexes, binders, pitch, and ink and combinations thereof. Stickies can also be classified as macrostickies or microstickies depending upon the size of the stickies.

Stickies may cause operational and product quality problems. Stickies can deposit on surfaces of the paper machine equipment, such as wires, felts, press rolls, and drying cylinders, cause process upsets, hinder fiber bonding, and reduce product quality. For instance, stickies may cause bright and dark spots in the paper or even sheet breaks, which results in lower paper quality, production losses and extra operating stops for cleaning. Consequently, it is necessary to monitor and control stickies to improve papermaking operations and product quality.

The amount of stickies in the recycled pulp may be reduced by, e.g., optimization of re-pulping parameters, cleaning and screening, flotation, dispersing and chemical treatment. Usual chemical treatments to reduce stickies or to reduce their sticky character are dispersion and/or passivation of the stickies by addition of e.g. talc and/or bentonite, chemical detacifiers, e.g. polymers, and treatment of the process equipments with chemicals to retard the deposition. These chemical treatments contribute significantly to operating costs.

In the art, the amount of micro- and macrostickies is usually determined using standard laboratory analytical procedures, e.g. extraction methods or laboratory screening. Per definition, microstickies are stickies that pass a 100 µm slotted plate in laboratory screening. Macrostickies are defined as the stickies in the residue of the 100 µm screen. The standard laboratory analytical procedures for determining sticky levels allow the determination of either micro-, macro- or both types of stickies.

For instance, macrostickies can be monitored using a device known as a "Pulmac shive analyzer" or "Haindl fractionator", which screens out the macrostickies from the furnish and determines the macrosticky level through image analysis. This process usually takes several hours to complete, and is useful as a retroactive control of the macrosticky level.

The use of near infrared (NIR) spectroscopy in combination with multivariate data analysis to determine the amount of stickies has also been suggested. For instance, Enrico Pigorsch and Petra Behnsen (PTS Heidenau, journal ATIP, vol. 64, no 4) have suggested online monitoring of microsticky load in the paper web by NIR measurements.

Most standard laboratory analytical procedures for determining stickies are, however, laborious and time consuming and do not allow a continuous monitoring of the sticky load in the pulp to be processed. Moreover, they are limited to the determination of stickies of a certain kind (i.e. stickies of a certain chemical nature or composition), e.g. hot melts, pressure-sensitive adhesives (PSAs), latexes, binders, pitch, or ink; or of a certain size (i.e. micro- or macrostickies). As a result, a single standard laboratory analytical procedure for determining stickies cannot explain all effects and problems that may be caused by stickies, since each procedure is based on a different measuring principle taking size and chemical properties of the stickies into account.

There does not appear to be any method or system for continuously and automatically determining sticky levels of "all" kinds of stickies in a process for producing recycled fibre pulp.

Consequently, there is a need for a comprehensive method for continuously and automatically determining sticky levels in a process for producing recycled fibre pulp. In particular, there is a need for a method that allows determining various kinds of stickies with a single measurement easily and efficiently.

DESCRIPTION OF THE INVENTION

The present invention relates to a method of continuously and automatically determining sticky levels in a process for producing recycled fibre pulp utilizing near-infrared (NIR) spectroscopy in combination with one or more automated sheet former(s), which comprises the steps:
(a) determining sticky levels for a series of samples using a standard laboratory analytical procedure, utilizing the results as reference values to establish one or more calibration model(s) from NIR spectroscopy, and storing the dataset(s) of the calibration model(s) on an electronic storage device;
(b) automatically withdrawing a sample from at least one sampling point in the process line, transporting the sample through a sample line from the process line to at least one automated sheet former, forming a sheet from said sample, and drying said sheet;
(c) transporting the dried sheet from step (b) to a measuring zone and recording a spectrum from the sheet in the near infrared region to obtain spectral data;

(d) processing the spectral data obtained in step (c) on a computer utilizing at least one stored calibration model, and receiving for each calibration model as output a value of the sticky level in the process for producing recycled fibre pulp.

The method of the invention makes it possible to monitor and control the amounts of stickies in real-time in the process of producing recycled pulp. The method allows the process of producing recycled pulp to be controlled in a feed-forward manner in order to reduce the amount of stickies and/or adjust the process to thereby minimize negative effects of the stickies on the production process, e.g. reject rates and/or chemical dosages.

The method can be used in any conventional process for producing recycled fibre pulp, which process, for example, comprises the steps of pulping recovered paper and cleaning the resulting fiber suspension, e.g. by screening, centrifugal cleaning and/or flotation.

The near infrared (NIR) calibration models may be established by calibrating reference spectral data, obtained by spectrometric measurements in the near infrared range on reference samples, to known sticky values of said reference samples by means of partial least squares regression.

Spectral measurements are made on the formed sheets by use of a NIR spectrometer, such as a Fourier Transform Near Infrared spectrometer. The spectrometer may comprise a fiber-coupled measurement head for contactless measurements on the sheet. Preferably, the spectral measurements are performed in the near-infrared spectral region, most preferably in the wavelength range of 833 to 2564 nm or 12000 to 3900 $cm^{-1}$. Spectral data is collected by means of transmission or reflectance for each formed sheet, preferably reflectance. In this way, spectral data is obtained for each sheet.

The NIR calibration models are elaborated by spectral measurements on reference samples with known sticky values and thereafter NIR calibration models are created by use of multivariate data analysis. The multivariate data analysis may be carried out using e.g. partial least squares regression (PLS). Multivariate analysis (MVA) is based on the statistical principle of multivariate statistics, which involves observation and analysis of more than one statistical outcome variable at a time. This statistical technique allows to take into account the effects of all variables on the responses of interest, e.g. data from different sampling points and/or machine and process parameters.

The known sticky values of the reference samples are the amounts of stickies in the samples as determined by means of standard laboratory analytical procedure for determining stickies, including reference methods such as Ingede method No. 4, Kaipola sticky method, extraction by means of dimethylformamide (DMF), tert-butyl methyl ether (TBME) or dichloromethane (DCM), flow cytometry, addition of deposits of the doctor blades of the paper machine to pulp samples, or addition of industrial adhesives to pulp samples.

The sticky values of the reference samples as determined by the individual standard laboratory analytical reference methods and the spectroscopic data of the reference samples are used as input for a correlation to create a calibration model for each standard laboratory analytical reference method. Accordingly, it is possible to predict stickies levels for various kinds of stickies by processing obtained spectroscopic data from a sample utilizing one or more calibration model(s). In other words, the spectroscopic data of a single NIR spectrum from a single sample can be utilized as input in one or more of the calibration models thereby yielding as output one or more sticky value(s) as determined with each of the respective laboratory analytical reference methods forming the basis of the individual calibration models.

It is also possible to combine the output data of the individual calibration models to create a second multivariate model, below referred to as second model. The second model can be used to predict or determine a value, which value expresses the adverse effects of the stickies on the production process, e.g. paper quality defects and/or problems at the paper machine, e.g. deposits on paper machinery, web breaks, holes and spots. This value of the second model is also referred to as sticky disturbing potential. Historical data of process conditions and machinery settings may also be used as additional values that can be taken into account for predicting the sticky disturbing potential, due to the fact that those parameters can affect the harmfulness of stickies, e.g. pH value and ash content of the pulp or temperature profiles of the drying cylinders of the paper machine.

A first sticky value may e.g. be determined by use of flow cytometry and a second sticky value may e.g. be determined by means of the Kaipola sticky method. Then the output data of these methods are combined and weighted according to their relative impact on the runability of the paper machine to thereby create a sticky disturbing potential. As outlined above, the different reference methods can express different types or different sizes of stickies. The impact of these different types or sizes of stickies on the runability of the paper machine depends, among other things, on prevailing process conditions, such as pH value and ash content of the pulp, temperature profiles of the drying cylinders of the paper machine. By weighting the different amounts of stickies depending on their impact on the runability of the paper machine and paper quality at prevailing process conditions, a sticky disturbing potential is achieved which reflects the actual problems caused by the stickies.

The weight of the sticky values predicted by means of different NIR calibration models on the runability of the paper machine/process may be determined by means of multivariate data analysis. This can, e.g., be accomplished by creating a second multivariate model wherein the weight of the variables expressing the amounts of stickies on parameters expressing e.g. number of breaks within a specific time period and/or deposits on the paper machinery is calculated. This may be accomplished by means of PLS. In this model, the variables expressing the amounts of stickies may be the predicted sticky values determined by means of the different NIR calibration models achieved by performing spectral measurements on the samples and applying the NIR multivariate calibration models on said spectral measurements. The second model may further comprise other process and pulp parameters, e.g. pH value and ash content of the pulp, temperature profiles of the drying cylinders of the paper machine.

The second model can be used to determine the sticky disturbing potential of new samples, collected on-line in the process as explained above. The predicted sticky disturbing potential values are thereafter used to regulate the process, e.g. by regulating the reject rates of screens or steering the amount of chemicals added to the fiber suspension.

The term "one or more" as used herein means an integer of from 1 to 50, preferably an integer of from 1 to 15, more preferably 1, 2, 3, 4, 5, 6, 7, or 8.

The method of the invention can also be characterized in that the method further comprises the step of measuring the weight of the sheet after recordation of the NIR spectrum.

The method of the invention can also be characterized in that the calibration model is established by calibrating reference spectral data, obtained by spectrometric measurements in the near infrared region on reference samples, to known sticky values of said reference samples by means of multivariate data analysis.

Further, the method of the invention can be characterized in that at least one sample from at least one sampling point in the process line is withdrawn every hour. Preferably at least one sample from at least one sampling point in the process line is withdrawn at least every 30 min, more preferably at least every 15 min, and most preferably about every 5 to 12 min. According to the method of the invention it is possible to withdraw individual samples at defined sampling points in the process line at certain time intervals, e.g. at least one sample per hour, at least one sample every 30 min, at least one sample every 5 to 15 min.

The method of the invention can also be characterized in that the process for producing recycled fibre pulp utilizing near-infrared (NIR) spectroscopy in combination with an automated sheet former comprises at least one of the following process steps: pulping, high density (HD) cleaning, pre-screening, high weight (HW) cleaning, intermediate consistency (IC) screening, pre-flotation, fine screening, thickening (i.e. water is removed from the pulp, e.g. using a disk filter), dewatering (i.e. water is removed from the pulp, e.g. by channeling the pulp through a screw press or double wire press), dispersion (i.e. thermo-mechanical treatment of the pulp to reduce the size of stickies), post-flotation, thickening, dewatering, stock tower (i.e. a tank located between a deinking plant and a paper machine where the deinked pulp is stored), or combinations thereof.

The method of the invention can also be characterized in that the process for producing recycled fibre pulp utilizing near-infrared (NIR) spectroscopy in combination with an automated sheet former has the following process arrangement: pulping, HD cleaning, pre-screening, HW cleaning, IC screening, pre-flotation, fine screening, thickening, dewatering, dispersion, post-flotation, thickening, dewatering, and stock tower, in that order.

According to the invention, a sample can be withdrawn from one or several sampling points in the process line. The sampling point in the process line can be selected from the sampling points: immediately downstream of the pre-screening, immediately downstream of the HW cleaning, immediately downstream of the IC screening, immediately downstream of the pre-flotation, immediately downstream of the fine screening, immediately downstream of the dispersion, immediately downstream of the post-flotation, immediately downstream of the stock tower. In this way, the reject rates can be controlled in a feed-forward manner.

One sample may, e.g., be withdrawn in advance of, i.e. upstream of, at least one screener. At this sampling point, the fiber suspension contains a large amount of macrostickies but also microstickies. A second sampling point may, e.g., be after the deinked pulp storage tower, wherein the fiber suspension contains still macro-, and microstickies but on a lower level. A third sampling point may be the head box of the paper machine, wherein the pulp suspension also contains secondary stickies. In one embodiment according to the invention, samples may be taken from a combination of sample points, e.g. the three sampling points mentioned above, with a certain time shift depending on the sheet former capacity.

The method of the invention can be characterized in that samples are withdrawn from at least two sampling points in the process line, more preferably from at least three sampling points in the process line. This makes it possible to monitor and control different kinds and sizes of stickies, e.g. macro- and microstickies, at different positions in the process line.

The method of the invention can be characterized in that a sample is withdrawn from the sampling point in the process line for recycled fibre pulp production located immediately downstream of the stock tower.

Preferably, the method utilizes one or more standard analytical procedure(s) to create (a) respective calibration model(s). Preferably, the standard analytical procedure(s) is/are selected from: Ingede method No. 4, Kaipola sticky method, extraction by means of dimethylformamide (DMF), tert-butyl methyl ether (TBME), or dichloromethane (DCM), flow cytometry, addition of deposits of the doctor blades of the paper machine to pulp samples, addition of industrial adhesives to pulp samples, or combinations thereof.

The INGEDE method 4 describes a laboratory screening procedure for pulps of a recovered paper treatment process. The reject of this screening procedure over a 100 μm slotted plate is prepared in such a way that the macro stickies can be determined by means of an image analysis system. The obtained values are the macro sticky area expressed as $mm^2$ per kg pulp. Specifically, the Ingede method No. 4 is an established method for the determination of macrostickies and a detailed description of the method is available at the Ingede web site (http://www.ingede.com/ingindxe/methods/ingede-method-04-2013.pdf, 09.04.2013). The method can be used to obtain reference sticky values employing a Haindl classifier according to ZM V/1.4/86 and a slotted plate with a nominal slot width of 100 μm (according to ZELLCHEMING Technical Leaflet RECO 1, "Anforderungen an die Güte von Schlitzplatten für Labor-Sortieraggregate" (engl.: "Quality Requirements of Slotted Plates for Laboratory Screening Devices"); www.zellcheming.de).

The Kaipola sticky method also describes a laboratory screening procedure but after screening the macro sticky area is determined by visual inspection, i.e. manual counting of stickies using a pattern for comparison of the size. The obtained value is the macro sticky area expressed by $mm^2$ per kg pulp. Specifically, the Kaipola sticky method comprises the following steps:

1. Pulp Preparation

If the consistency of the sample determined according to DIN EN ISO 4119 is above 2% the pulp is disintegrated in lab disintegrator according to ISO 5263-1. The disintegration of 50 g bone dry pulp is performed at 3000 rpm and 2% consistency for 10 minutes. Otherwise the fibre flakes may disturb the screening. After disintegration the pulp is filled up to 5 liters with tap water.

2. Screening

The screening is done with a Somerville screen (TAPPI T 275 sp-07), in which 50 g bone dry pulp are screened for 20 minutes with a 100 μm slotted plate. The residual over the screen plate is transferred to a white filter paper of 110 mm diameter, covered with an aluminum foil, loaded with a heated metal plunger (130 mm diameter, 2.8 kg) and dried on an oven plate. The temperature of the plate is 100 to 110° C. and drying is performed until the filter paper becomes slightly brown, which takes about 10 minutes. Additional white filter papers should be used if there is an overlapping of residuals on the filter paper. This means the residues of the slotted plate have to be split up to more than one filter paper before drying them.

3. Sticky Determination

Figure 10:
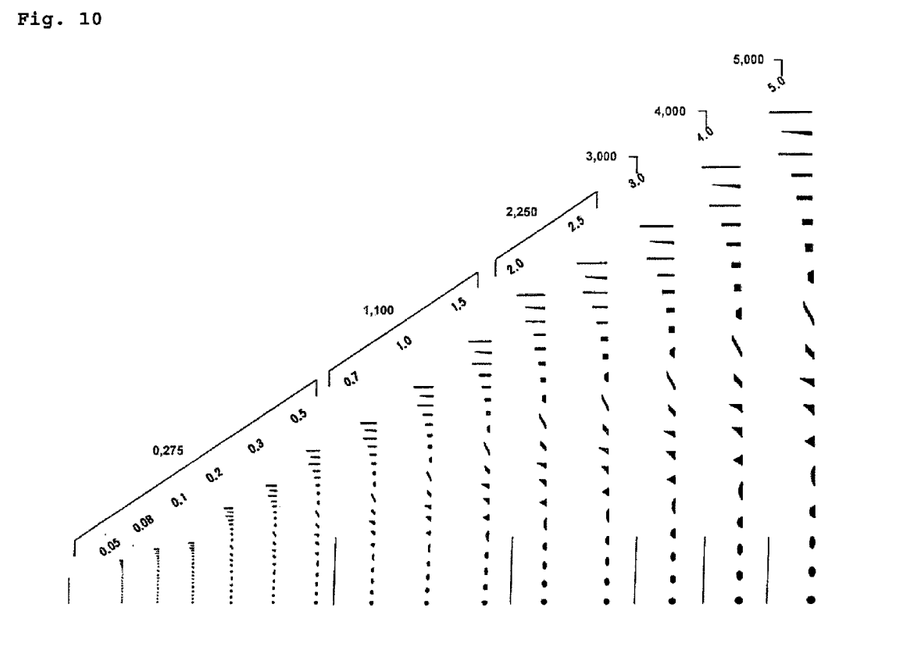
FIG. 10 shows a pattern (scaled) for manually determining the sticky amount. The pattern is put on a transparent reference foil and the sticky amount (white spots) is estimated by manually determining the number and size of stickies in a pulp sample using said transparent foil.

The aluminum foil is released after the drying. A rewetting of the filter paper, on which the residuals are located, is done with tap water. The wet filter paper is placed on a black surface on which the stickies are visible as white spots. The sticky amount (white spots) is estimated by numbers and size manually using the transparent reference foil shown in FIG.

10 (scaled). The transparent foil is placed over the wetted filter paper and the stickies are classified and compared with the areas on the foil according to Table A below. The number of stickies per class is cumulated and multiplied by the average area of each size class of stickies. The result is then multiplied by 20 to obtain the sticky area per kg pulp.

TABLE A

Sticky evaluation with reference foil

| Group No. | Area of stickies (mm$^2$) | Average area of size class of stickies (mm$^2$) |
|---|---|---|
| 1 | 0.05 to 0.50 | 0.275 |
| 2 | 0.70 to 1.50 | 1.100 |
| 3 | 2.00 to 2.50 | 2.250 |
| 4 | 3.00 | 3.000 |
| 5 | 4.00 | 4.000 |
| 6 | 5.00 | 5.000 |

By means of flow cytometry the number and particle size distribution of small hydrophobic particles are determined by scattering of laser light in a flow-through cell after dying of hydrophobic particles using fluorescent agents. In particular, flow cytometry can be used to measure the fluorescence of particles in a size range of about 035 µm up to 100 µm. For the measurement of hydrophobic sticky particles staining with nile red is used. Nile red stains hydrophobic particles like micro stickies in fibre suspensions in a preferred way compared to more hydrophilic fibres and fillers. Flow cytometry comprises the following steps:
1. Determination of the consistency of the process sample according to DIN EN ISO 4119.
2. 400 ml of the process sample of step 1 are taken and diluted to 1% consistency using tap water. The dilution is performed under stirring conditions (e.g. stirring by hand with a glass stirrer).
3. The diluted sample of step 2 is in a first step filtrated with a Britt Dynamic Drainage Jar (BDDJ) using a metal screen of 150 mesh according to a hole diameter of 106 µm and in a second filtration step the sample is fine screened using a 80 µm hole diameter filter in order not to plug the cuvette of the flow-cytometer.
4. The filtrate of step 3 is diluted by ten times (1:10) using Milli-Q-water to obtain a base dilution. A test sample of 1 ml is prepared by mixing 50 µl of the base dilution with 950 µl Milli-Q-water in a cuvette (i.e. a further dilution of 1:20). 20 µl nile red (0.001% in methanol) is added to the test sample to obtain a cuvette sample. The cuvette sample is stored in darkness for a reaction time of 5 minutes. Directly before measurement the cuvette sample is mixed with a vortex generator (e.g. TopMix FB15024 (Fisher Scientific)) for 15 seconds at an intensity of 25 Hz to ensure a homogeneous sample. The count rate of the cuvette sample is adjusted to 900-1100 counts/sec in a flow-cytometer (if the cuvette sample does not have a count rate of 900-1100 counts/sec, the base dilution needs to be adapted accordingly to achieve a count rate of 900-1100 counts/sec and the measurement has to be repeated).
5. The total amount of hydrophobic sticky particles in the cuvette sample of step 4 is determined with a flow-cytometer, e.g. Cyflow SL® (by Partec) equipped with a 488 nm blue solid state laser and 5 optical parameters (forward scatter (FSC), side scatter (SSC), detector sensitive for wave length of green light (FL1), detector sensitive for wave length of orange light (FL2), detector sensitive for wave length of red light (FL3)) using the parameter settings shown in Table B.

The measuring time is approximately 180-220 seconds measuring a constant volume of 0.2 ml. About 200.000 particles are recorded with these settings. The FSC channel is used as triggering channel with a sample flow speed of 2.5 µl/sec.

TABLE B

Flow-cytometer settings for measuring of hydrophobic particles

| Parameter | Label | Gain | Log | Low limit | Upper limit |
|---|---|---|---|---|---|
| FSC | Forward | 98 | log 4 | 50 | 999.9 |
| SSC | Side | 120 | log 4 | 10 | 999.9 |
| FL1 | Green | 320 | log 4 | 10 | 999.9 |
| FL2 | Orange | 370 | log 4 | 10 | 999.9 |
| FL3 | Red | 320 | log 4 | 10 | 999.9 |

Extraction methods deliver the amount of pulp components soluble in appropriate solvents, e.g. dimethylformamide (DMF), tert-butyl methyl ether (TBME) or dichloromethane (DCM) expressed as percentage of soluble material. Specifically, extractions of soluble organic materials can be performed according to DIN EN ISO 14453 (December 1998) using dimethylformamide (DMF) and tert-butyl methyl ether (TBME) instead of acetone or dichloromethane (DCM; DCM needs to be replaced due to its harmful properties and legislation in some countries).

The addition of industrial adhesives to pulp samples was used as another method for sample preparation for NIR modelling. A mixture of common hot melts, dispersion glues and starch/dextrine/casein glues was applied to paper, mixed properly and added to pulp samples with a mass share of 0 to 10 percent whereof sheets were formed. Specifically, different types of commonly used adhesives in the paper industry were purchased from adhesive producers and applied to standard newsprint paper. The newsprint paper with the applied adhesives was covered with another sheet of standard newsprint paper, loaded with a metal plate and dried for two hours in an oven at 105° C. The types of adhesives and their relative share in the adhesive application mixture are shown in Table C. The adhesive application mixture was composed and mixed with a hand blender at 20% consistency for 10 minutes in order to achieve a homogeneous mixture of adhesives and pulp.

TABLE C

Adhesive application mixture

| Adhesive type | share in mixture [%] |
|---|---|
| Dispersion | 40.4 |
| Hot melts | 22.2 |
| Casein | 12.1 |
| Starch/dextrin | 11.1 |
| PUR-Hot melts | 9.1 |
| Latex | 5.1 |

Standard newsprint paper was then pulped using a Hobart pulper at 20% consistency with addition of 0.6% NaOH, 1.8% silicate and 0.7% peroxide. The share of adhesives relative to the pulp was defined (0 to 10%) and the needed amount of adhesive application mixture was calculated and mixed properly with the pulped newsprint paper. Subsequently funnel sheets were formed and dried as described in the INGEDE method 1 (http://www.ingede.com/ingindxe/methods/ingede-method-01-2007.pdf). After drying those funnel sheets with known content of adhesives were used for the elaboration of an NIR calibration model.

Deposits of the doctor blades of the paper machine were cooled down by using liquid nitrogen, crushed and then added to pulp samples with a mass share of 0 to 20 percent whereof sheets were formed for spectroscopic measurements. In particular, deposits of the doctor blades of the paper machine were collected. Due to the sticky properties the deposits were cooled down with liquid nitrogen to make the material more brittle and to be able to reduce the particle size. The sample was treated mechanically by using a standard porcelain mortar with continuous addition of liquid nitrogen to keep the temperature on a low level for about 15 minutes. The prepared sample material with particle sizes of 150 to 500 μm was then kept in a freezer at −20° C. to prevent re-agglomeration of the particles. Standard newsprint paper was pulped using a Hobart pulper at 20% consistency with addition of 0.6% NaOH, 1.8% silicate and 0.7% peroxide. Defined masses of the deposits (0 to 20% related to the funnel sheet weight) were then added to the pulp suspension and stirred properly. Subsequently funnel sheets were formed and dried as described in the INGEDE method 1 (http://www.ingede.com/ingindxe/methods/ingede-method-01-2007.pdf). After drying those funnel sheets with known content of deposits of the doctor blades of the paper machine were used for the elaboration of an NIR calibration model.

The NIR calibration models are validated by use of reference samples with known content of stickies as determined by one or more standard analytical procedure(s).

The method of the invention can further be characterized in that the method further comprises a step for controlling the sticky levels in the process for producing recycled fibre pulp from recovered paper based on the determined value of the sticky levels according to step (d).

Additionally, the method can be characterized in that the step for controlling the sticky levels in the process for producing recycled fibre pulp from recovered paper comprises: adjusting the reject rate of at least one screener, regulating the operating conditions of the pre- or post-flotation, adjusting the disperser settings (i.e. changing the mechanical energy that is put in the pulp by using a rotor and stator equipped with teeth, e.g. by closing or opening the gap between rotor or stator; or by changing the consistency of the pulp) and/or steering the amount of chemicals added to the fiber suspension (i.e. increasing or decreasing the amount of chemicals added in relation to the amount of stickies; for example, if the sticky amount is very low, the amount of chemicals can be reduced thereby saving costs and preserving the environment), which chemicals have an effect of passivation, stabilisation, detackification, fixation or reducing the content of the stickies in the pulp.

The invention further pertains to a system for continuously and automatically determining sticky levels in a process for producing recycled fibre pulp utilizing near-infrared (NIR) spectroscopy in combination with an automated sheet former according to the method described above, comprising: at least one automated sheet former to form a sheet of sample(s) taken from at least one sampling point in the process line; one or more means for transporting the sample through sample line(s) from the process line to the at least one automated sheet former; one or more transportation means for transporting the sheet from a sheet former to a measuring zone for recording a spectrum from the sheet in the near infrared region; a spectrometer to perform spectroscopic measurements on the formed sheets in the NIR region; and a computer programmed to carry out multivariate data analysis.

The system according to the invention makes it possible to continuously and automatically monitor the amount of stickies in the fiber suspension in real-time. Moreover, the method and system of the invention allow simultaneous determination of values for various kinds of stickies by processing the spectral data obtained for the individual sample(s) of the process for producing recycled fibre on a computer utilizing one or more of the calibration models, alone or in combination.

The invention is now further explained by way of example.

EXAMPLES

1. Development of the NIR Calibration Models (to be Further Used to Predict Values of Process Samples and to Calculate the Sticky Disturbing Potential Value)

Several reference pulp samples and validation samples were withdrawn from the process; all samples were taken along the deinking process to cover a wide range of amounts of stickies, ash and ink content, e.g. after coarse screening, inlet and outlet screening stages, final pulp etc. Table 1 shows the number of reference pulp samples used for each NIR calibration model. The amounts of stickies in said samples were determined using flow cytometry, DMF extraction, TBME extraction, Ingede method No. 4, turbidity measurement, Kaipola sticky method, mixing of paper machine deposits and adhesives into pulp giving rise to eight different values expressing the amounts of stickies in each sample, i.e. eight variables per sample that are to be correlated to NIR measurements. The results of said measurements are shown in Table 1 below.

Reference sheets and validation sheets were made of the pulp samples either by means of an automated sheet former supplied by Techpap or offline by means of a Büchner funnel. NIR measurements were carried out on said sheets using a MATRIX-F fibre based emission FT-NIR spectrometer supplied by Bruker Optik GmbH. 3 spectra were taken in a spectral range of 12000 to 3900 cm$^{-1}$ with a resolution of 4 cm$^{-1}$ for each reference sample.

The calibration models based on the NIR measurements of said reference samples and the measured amounts of stickies were created by means of PLS using the software OPUS supplied by Bruker Optik GmbH. For each sticky reference method two separate NIR calibration models were established using different spectral pre treatment methods and spectral ranges (below referred to as version 1 (V1) and version 2 (V2). The calibration models were tested using an internal cross validation and external validation sets.

The internal validation of the NIR calibration models was done using a leave-out-one-cross-validation. The coefficient of determination and the root mean square error of cross validation (RMSECV) are shown in Table 1.

TABLE 1

Reference samples and results of internal validation

| NIR Model | No. of spectra | $R^2$ | RMSECV | Unit | Rank |
|---|---|---|---|---|---|
| DMF V1 | 275 | 95.5 | 0.040 | % | 8 |
| DMF V2 | 419 | 97.9 | 0.045 | % | 10 |
| FCM V1 | 96 | 90.1 | 26400 | part/ml | 7 |
| FCM V2 | 369 | 94.3 | 25000 | part/ml | 9 |
| Kaipola V1 | 116 | 88.1 | 227 | mm$^2$/kg | 7 |
| Kaipola V2 | 131 | 85.5 | 245 | mm$^2$/kg | 10 |
| Ingede 4 V1 | 178 | 87.3 | 266 | mm$^2$/kg | 6 |
| Ingede 4 V2 | 293 | 86.3 | 160 | mm$^2$/kg | 8 |
| Adhesives V1 | 87 | 93.1 | 0.359 | % | 7 |
| Adhesives V2 | 101 | 89.7 | 0.453 | % | 8 |
| Deposits V1 | 143 | 90.6 | 0.575 | % | 4 |
| Deposits V1 | 127 | 90.8 | 0.547 | % | 6 |
| Turbidity V1 | 83 | 81.9 | 0.069 | NTU | 8 |
| Turbidity V2 | 82 | 81.3 | 0.071 | NTU | 8 |
| TBME V1 | 134 | 85.4 | 0.022 | % | 5 |
| TBME V2 | 193 | 81.8 | 0.025 | % | 9 |

The external validation was done by taking 55 pulp samples from the process and predicting the sticky values applying the NIR calibration models. The coefficients of determination are shown in Table 2 below. With the exception of the INGEDE 4 V2 NIR calibration model, all models show a good coefficient of determination.

TABLE 2

External validation results

| NIR Model | No. of spectra | $R^2$ | Unit |
|---|---|---|---|
| DMF V1 | 55 | 94.1 | % |
| DMF V2 | 55 | 96.8 | % |
| FCM V1 | 55 | 92.8 | part/ml |
| FCM V2 | 55 | 78.2 | part/ml |
| Kaipola V1 | 55 | 77.3 | mm$^2$/kg |
| Kaipola V2 | 55 | 70.3 | mm$^2$/kg |
| Ingede 4 V1 | 55 | 93.4 | mm$^2$/kg |
| Ingede 4 V2 | 55 | −7.0 | mm$^2$/kg |
| TBME V1 | 55 | 67.1 | % |
| TBME V2 | 55 | 90.8 | % |

2. Development of a Second Model to Determine a Sticky Disturbing Potential Value Over a period of about four month the automated sheet former and the NIR spectrometer were used for on-line data collection; continuously four to five samples per hour were taken from outlet deinked pulp storage tower to the paper machine. The different NIR calibration models were used to predict the amounts of stickies according to different reference methods in each of the process samples. The predicted values were transferred to the mill wide information and production quality control system for later data evaluation.

Simultaneously as the pulp samples were withdrawn from the outlet deinked pulp storage tower, various runability parameters of the paper machine were monitored e.g. the number of breaks at the paper machine, holes and spots in the paper, paper machine speed. Beside those mentioned parameters for the runability of the paper machine also process parameters of the paper machine and deinking process including recovered paper quality were monitored by on-line sensors or manually, e.g. ash content, pH values, production rate and settings of machineries.

Figure 1:
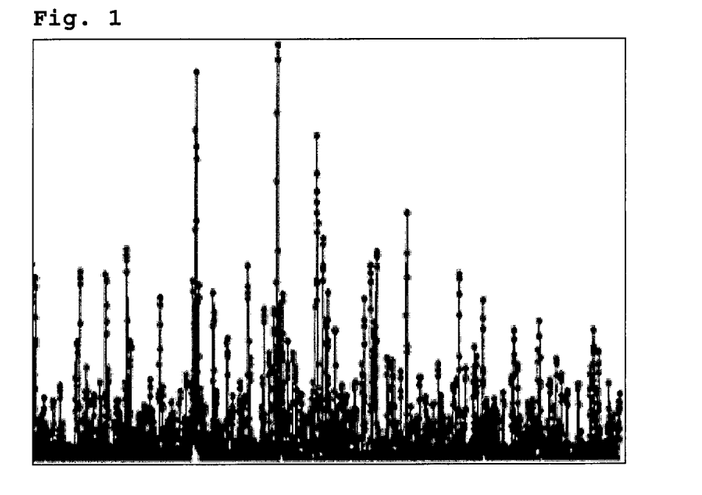
FIG. 1 shows a graphic representation of single values of bright and dark spots observed in the production of a paper over a certain time period.
Figure 2:
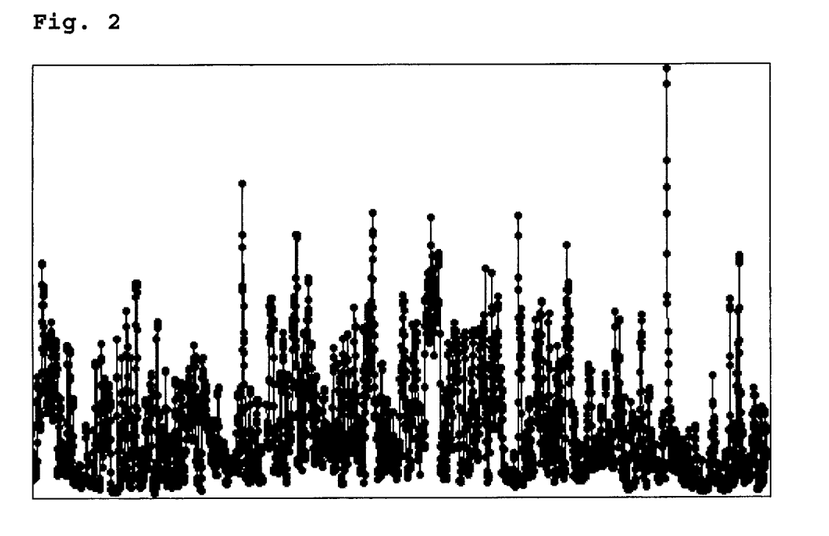
FIG. 2 shows a graphic representation of breaks observed in the production of a paper over a certain time period.
Figure 3:
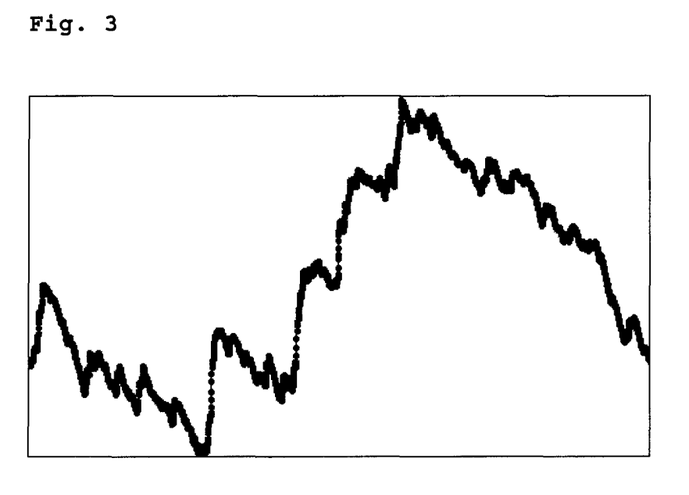
FIG. 3 shows a CUSUM chart created for the values of bright and dark spots depicted in FIG. 1.
Figure 4:
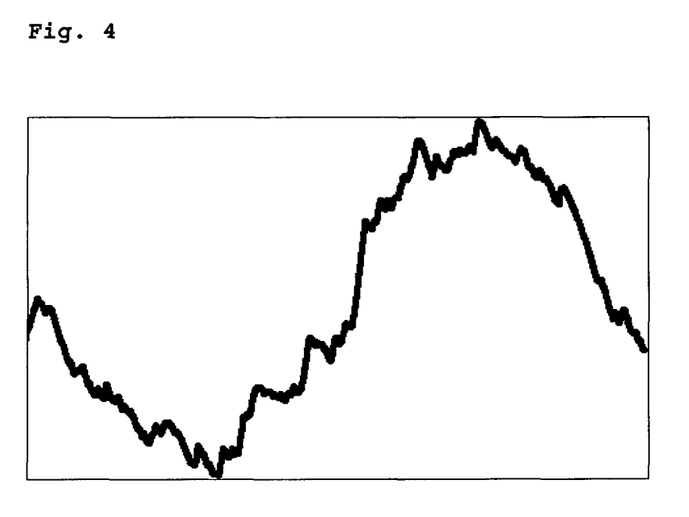
FIG. 4 shows a CUSUM chart created for the breaks depicted in FIG. 2.

A sticky disturbing potential as indicator for the runability of the paper machine had to be defined. The sticky disturbing potential is a value which expresses the adverse effects of the stickies on the production process, e.g. paper quality defects and/or problems at the paper machine, e.g. deposits on paper machinery, web breaks, holes and spots. The number of breaks is non-normal distributed and shows a high variation (Figure) thus using single values for the number of web breaks per day as sticky disturbing potential did not result in a good model. Bright and dark spots in the paper are monitored continuously (FIG. 1) and expected to correlate with the number of web breaks based on experience. Thus the number of breaks at the paper machine and the number of bright and dark spots were transformed using the CUSUM method to be able to correlate changes of those values. In statistical quality control, the CUSUM (or cumulative sum control chart) is a sequential analysis technique developed by E. S. Page of the University of Cambridge. It is typically used for monitoring change detection. By using this method the number of breaks could be correlated to the number of bright and dark spots in the same time period using historical data as shown in FIG. 3 and FIG. 4. A very good correlation could be observed.

Historical data of the single values of the on-line predicted amounts of stickies for each time period were correlated to the command variable bright and dark spots (CUSUM) by means of multivariate data analysis to determine the influence of each sticky value and process parameter on the runability of the paper machine.

Figure 5:
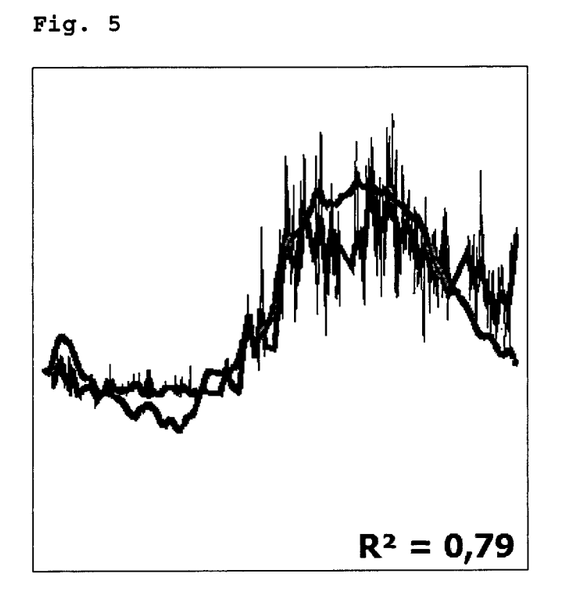
FIG. 5 shows a correlation of predicted sticky values according to the calibration model Adhesives V2 to the number of bright and dark spots observed in the production of a paper.
Figure 6:
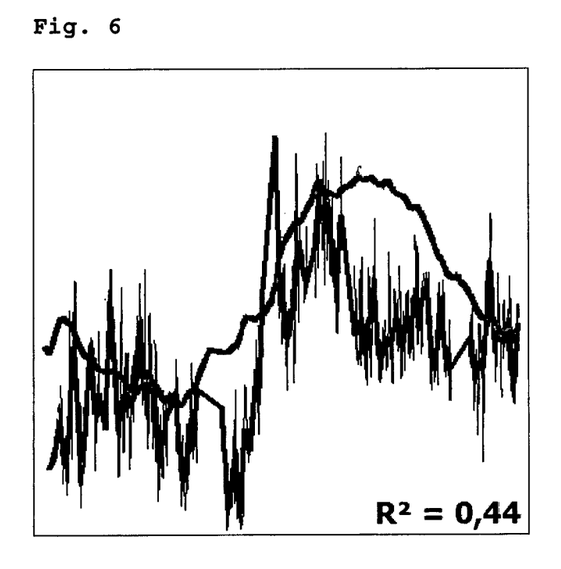
FIG. 6 shows a correlation of predicted sticky values according to the calibration model FCM V1 to the number of bright and dark spots observed in the production of a paper.
Figure 7:
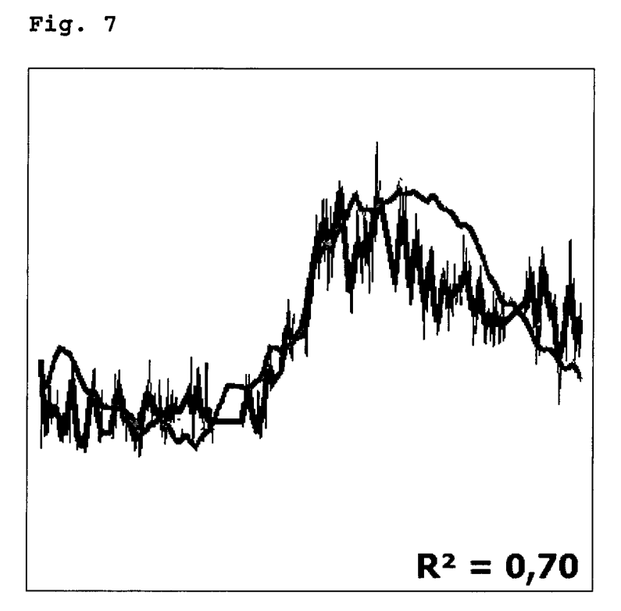
FIG. 7 shows a correlation of predicted sticky values according to the calibration model Deposits V1 to the number of bright and dark spots observed in the production of a paper.

As an example FIG. 5, FIG. 6 and FIG. 7 show the correlation of three single sticky values and the number of bright and dark spots (CUSUM) created using the software Minitab supplied by ADDITIVE GmbH. As expected, the correlation of a single method is not perfect.

Figure 8:
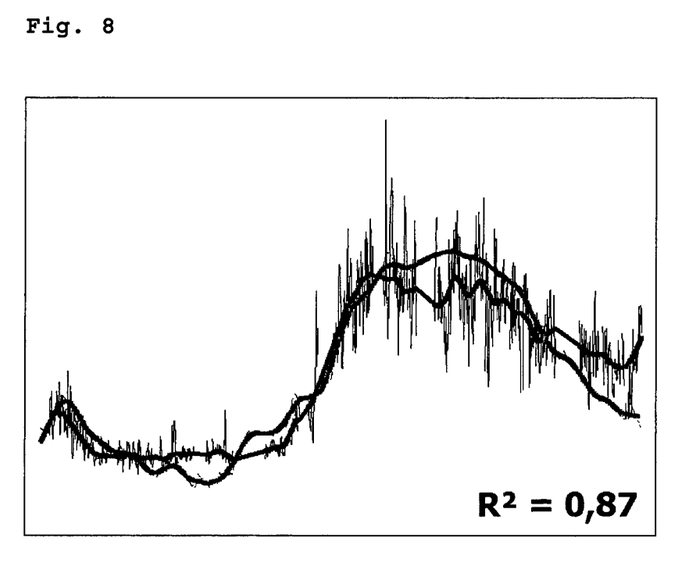
FIG. 8 shows a correlation of the combined sticky values according to the calibration models FCM V1 and Adhesives V2 to the number of bright and dark spots observed in the production of a paper.

The combination of more than one sticky value was investigated. FIG. 8 shows the improvement when the predicted values FCM V1 and Adhesives V2 are taken into consideration. The coefficient of determination is 0.87, and thus a very good prediction of bright and dark spots in the paper which is correlating to the number of breaks at the paper machine is possible just by using the above mentioned combination of sticky values.

Since the runability of the paper machine is affected by many parameters beside stickies, e.g. process conditions and machinery settings, e.g. pH value, ash content of the pulp, temperature profiles of the drying cylinders of the paper machine, those parameters were also included in the multivariate data analysis. Based on experience of the personnel at the mill, several parameters were included in the modelling. Starting with many potential influences, those parameters showing the most significant influence on the runability of the paper machine were determined by using the statistical software Minitab®.

The sticky disturbing potential expressing the weighted mean of amounts of stickies and process parameters (second model) can be calculated using a quadratic polynomial, wherein the individual sticky values and process parameters each represent a variable $x_1, x_2, x_3 \ldots, x_n$. The corresponding quadratic polynomial function p in n variables $x_1, \ldots, x_n$ is represented by the following equation 1:

$$p(x_1, x_2, \ldots, x_n) = a + \sum_{i=1}^{n} b_i \cdot x_i + \sum_{\substack{i=1 \\ j>i}}^{n-1} c_{ij} \cdot x_i \cdot x_j + \sum_{i=1}^{n} d_i \cdot x_i^2 \quad \text{Equation 1}$$

wherein a represents the coefficient of the constant term, $b_i$ represent coefficients of the linear terms, $c_{ij}$ represent coefficients of the coupling terms, and $d_i$ represent coefficients of the quadratic terms.

For example, the sticky disturbing potential in relation to "bright and dark spots" (=the CUSUM "bright and dark spots") can be calculated using the following sticky values and process parameters as variables: x1=the amount of stickies determined by means of method FCM V1 [part/ml], x2=the amount of stickies determined by means of method Adhesives V2 [%], x3=the volume flow of backwater to dissolved air flotation paper machine [l/s], x4=the chemical dosage of fixative to the machine chest [g/t], x5=the chemical dosage of fixative to the stock tower [g/t], x6=the set point pressure difference of drying section four and three at the paper machine [kPa] and x7=the set point pressure of drying section three at the paper machine [kPa]. The corresponding quadratic polynomial function reads as follows:

CUSUM "bright and dark spots"=43604.2+
0.0116883*FCM V1+10880.4*Adhesives
V2+19.4996*backwater to DAF+4030.08*pressure difference section 4 and 3−1381.25*pressure drying section 3+92.8893*fixative to machine chest+305.329*fixative to stock tower−
73.5915*Adhesives V2*Adhesives
V2−3.10093*pressure drying section 3*pressure drying section 3−0.577907*fixative to machine chest*fixative to machine chest−0.691416*fixative to stock tower*fixative to stock tower+
0.0120571*FCM V1*Adhesives
V2−25.1457*Adhesives V2*pressure drying section 3+2.45825*Adhesives V2*fixative to machine chest−15.8630*Adhesives V2*fixative to stock tower−47.9959*pressure difference section 4 and 3*pressure drying section 3+0.847618*fixative to machine chest*fixative to stock tower.

Figure 9:
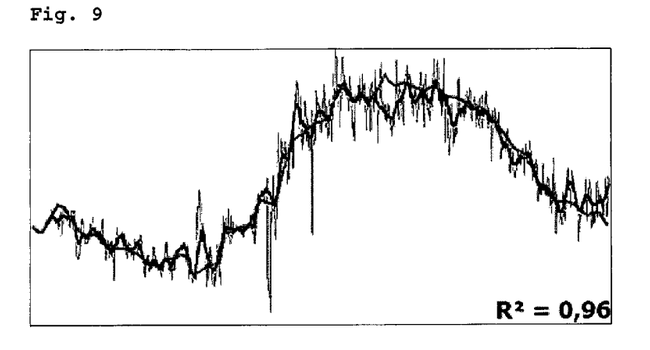
FIG. 9 shows a correlation of predicted values (intensely serrated grey line) and measured values (dark zigzag line) for bright and dark spots observed in the production of a paper.

A correlation between the measured and calculated bright and dark spots using the second model described above is shown in FIG. 9.

Accordingly, the second model can be used to determine the sticky disturbing potential of the current process conditions, and thus is a tool to improve the runability of the paper machine. In other words, the runability of the paper machine can be improved by considering the influence of single parameters on the creation of bright and dark spots in the paper, i.e. breaks at the paper machine, and by adjusting the process conditions or chemical additions to counteract a high sticky disturbing potential.

The invention has been described by way of examples, which are merely illustrative of the present invention and demonstrate application of the present invention as well as the benefits associated therewith. It is, however, to be understood that the invention is not to be limited to the examples. The invention is therefore intended to cover various modifications and equivalent arrangements included within the spirit and scope of the appended claims.

The invention claimed is:

1. A method of continuously and automatically determining sticky levels in a process for producing recycled fibre pulp utilizing near-infrared (NIR) spectroscopy in combination with one or more automated sheet former(s), which comprises the steps:
   (a) determining sticky levels for a series of samples using a standard laboratory analytical procedure, utilizing the results as reference values to establish one or more calibration model(s) from NIR spectroscopy, and storing the dataset(s) of the calibration model(s) on an electronic storage device;
   (b) automatically withdrawing a sample from at least one sampling point in a process line, transporting the sample through a sample line from the process line to at least one automated sheet former, forming a sheet from said sample, and drying said sheet;
   (c) transporting the dried sheet from step (b) to a measuring zone and recording a spectrum from the sheet in the near infrared region to obtain spectral data;
   (d) processing the spectral data obtained in step (c) on a computer utilizing at least one of the stored calibration models of (a), and receiving for each calibration model as output a sticky level value for the sample of (b) in the process for producing recycled fibre pulp.

2. The method according to claim 1, characterized in that the method further comprises the step of measuring the weight of the sheet after recordation of the NIR spectrum.

3. The method according to claim 1, characterized in that the calibration model is established by calibrating reference spectral data, obtained by spectrometric measurements in the near infrared region on reference samples, to known sticky values of said reference samples by means of multivariate data analysis.

4. The method according to claim 1, characterized in that at least one sample from at least one sampling point in the process line is withdrawn every hour.

5. The method according to claim 1, characterized in that the process for producing recycled fibre pulp utilizing near-infrared (NIR) spectroscopy in combination with an automated sheet former comprises at least one of the following process steps: pulping, high density (HD) cleaning, pre-screening, high weight (HW) cleaning, intermediate consistency (IC) screening, pre-flotation, fine screening, thickening, dewatering, dispersion, post-flotation, thickening, dewatering, stock tower, or a combination thereof.

6. The method according to claim 1, characterized in that the process for producing recycled fibre pulp utilizing near-infrared (NIR) spectroscopy in combination with an automated sheet former has the following process arrangement: pulping, high density (HD) cleaning, pre-screening, high weight (HW) cleaning, intermediate consistency (IC) screening, pre-flotation, fine screening, thickening, dewatering, dispersion, post-flotation, thickening, dewatering, and stock tower, in that order.

7. The method according to claim 6, characterized in that the at least one sampling point in the process line is: immediately downstream of the pre-screening, immediately downstream of the HW cleaning, immediately downstream of the IC screening, immediately downstream of the pre-flotation, immediately downstream of the fine screening, immediately downstream of the dispersion, immediately downstream of the post-flotation, or immediately downstream of the stock tower.

8. The method according to claim 1, characterized in that a samples is withdrawn from at least two sampling points in the process line.

9. The method according to claim 1, characterized in that a sample is withdrawn from the sampling point in the process line for recycled fibre pulp production located immediately downstream a stock tower.

10. The method according to claim 1, characterized in that the standard laboratory analytical procedure is selected from: Ingede method No. 4; Kaipola sticky method; extraction by means of dimethylformamide (DMF), tert-butyl methyl ether (TBME), or dichloromethane (DCM); flow cytometry; addition of deposits of doctor blades of a paper machine to pulp samples; or addition of industrial adhesives to pulp samples.

11. The method according to claim 1, characterized in that a sample is withdrawn from at least three sampling points in the process line.

12. A method for producing recycled fibre pulp from recovered paper, which comprises the steps:
   (a) determining sticky levels for a series of samples using a standard laboratory analytical procedure, utilizing the results as reference values to establish one or more calibration model(s) from NIR spectroscopy, and storing the dataset(s) of the calibration model(s) on an electronic storage device;
   (b) automatically withdrawing a sample from at least one sampling point in a process line, transporting the sample through a sample line from the process line to at least one automated sheet former, forming a sheet from said sample, and drying said sheet;
   (c) transporting the dried sheet from step (b) to a measuring zone and recording a spectrum from the sheet in the near infrared region to obtain spectral data;
   (d) processing the spectral data obtained in step (c) on a computer utilizing at least one of the stored calibration models of (a), and receiving for each calibration model as output a sticky level value for the sample of (b) in the process for producing recycled fibre pulp; and
   (e) controlling the sticky levels of the recycled fibre pulp from recovered paper based on the determined value of the sticky levels according to step (d).

13. The method according to claim 12, characterized in that the step for controlling the sticky levels in the process for producing recycled fibre pulp from recovered paper comprises: adjusting a reject rate of at least one screener, regulating operating conditions of a pre- or post-flotation, adjusting disperser settings or steering an amount of chemicals added to a fiber suspension, which chemicals have an effect of passivation, stabilisation, detackification, fixation or reducing the content of the stickies in the pulp.

* * * * *